United States Patent [19]

Rachlin

[11] Patent Number: 4,925,300

[45] Date of Patent: May 15, 1990

[54] OPTICAL FINGERPRINT IMAGING DEVICE

[76] Inventor: Daniel J. Rachlin, 2251 Williams St., Palo Alto, Calif. 94306

[21] Appl. No.: 227,558

[22] Filed: Aug. 2, 1988

[51] Int. Cl.$^5$ .......................... G06K 9/20; G06K 9/28
[52] U.S. Cl. .......................................... 356/71; 354/62
[58] Field of Search .......................... 356/71; 382/4, 5; 354/62

[56] References Cited

U.S. PATENT DOCUMENTS

| | | | |
|---|---|---|---|
| 2,730,936 | 1/1956 | Fagan et al. | |
| 2,817,996 | 12/1957 | Meyest | |
| 2,892,948 | 6/1959 | Frantz | |
| 3,200,701 | 8/1965 | White | |
| 3,529,520 | 9/1970 | Thiebault | 355/47 |
| 3,648,240 | 3/1972 | Jacoby et al. | 355/47 |
| 3,906,520 | 9/1975 | Phillips | 354/62 |
| 3,975,711 | 8/1976 | McMahon | 356/71 |
| 4,120,585 | 10/1978 | DePalma et al. | 356/71 |
| 4,152,056 | 5/1979 | Fowler | 354/62 |
| 4,322,163 | 3/1982 | Schiller | 356/71 |
| 4,428,670 | 1/1984 | Ruell et al. | 356/71 |
| 4,537,484 | 8/1985 | Fowler et al. | 354/62 |
| 4,544,267 | 10/1985 | Schiller | 356/71 |
| 4,553,837 | 11/1985 | Marcus | 356/71 |
| 4,557,559 | 10/1985 | Zimring | 356/243 |
| 4,569,080 | 2/1986 | Schiller | 356/71 |
| 4,581,760 | 4/1986 | Schiller et al. | 382/4 |
| 4,792,226 | 12/1988 | Fishbine et al. | 356/71 |

FOREIGN PATENT DOCUMENTS 0638249 4/1962 Italy .

OTHER PUBLICATIONS

Folette et al., *IBM Technical Disclosure* Bulletin (1974) 10(11).

*Primary Examiner*—Vincent P. McGraw
*Attorney, Agent, or Firm*—Irell & Manella

[57] ABSTRACT

Apparatus suitable for imaging fingerprints directly from a finger in contact with a transparent surface of a lens is described. The conical nature of the contact surface affords the opportunity for a single such surface to accommodate a wide range of finger sizes. The front surface of the lens is conical, and a light source is provided for illuminating the finger, with ridges of the fingerprint being imaged and light illuminating the papillary valleys being refracted away from the imaging means.

11 Claims, 7 Drawing Sheets

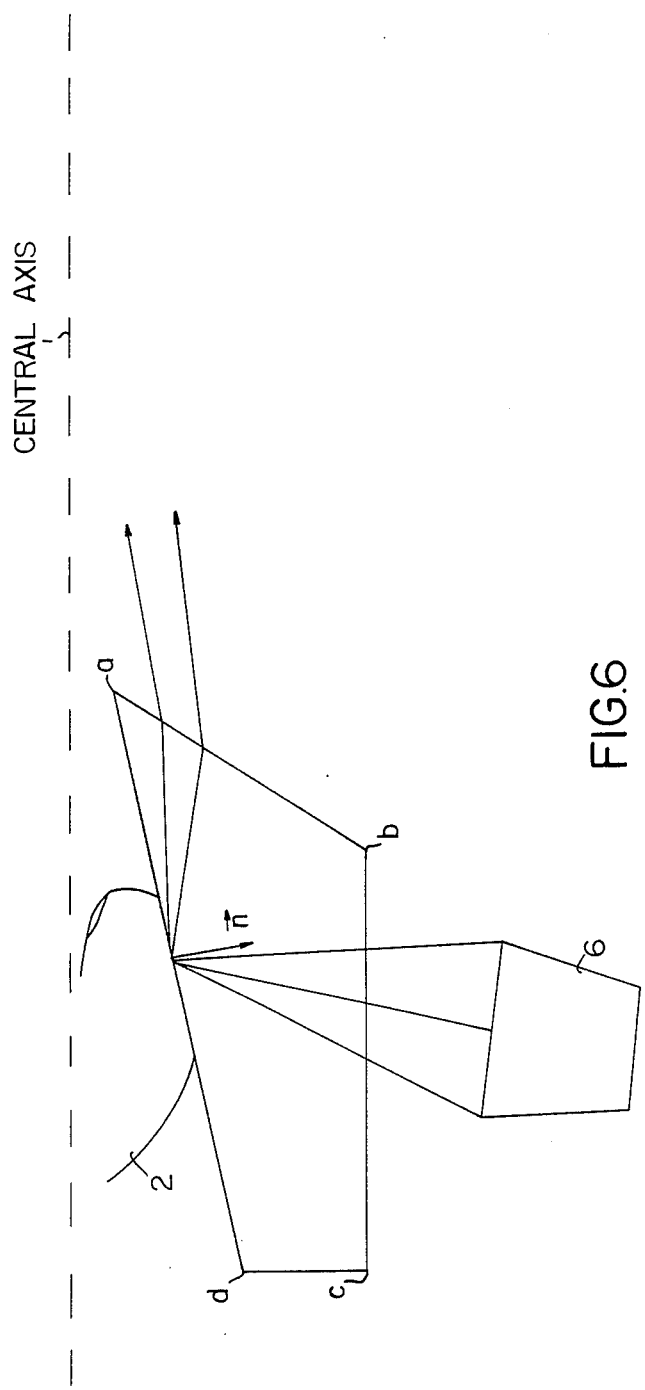

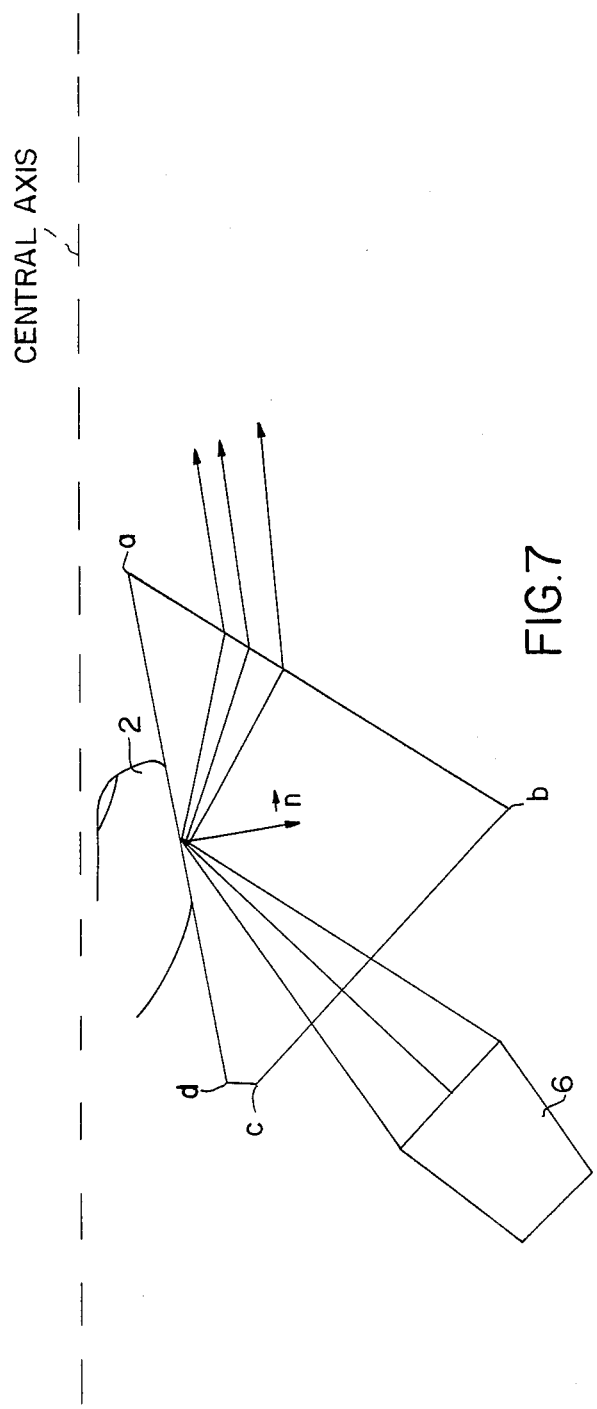

OPTICAL FINGERPRINT IMAGING DEVICE

BACKGROUND OF THE INVENTION

This invention addresses the need for providing a distortion-free image of a rounded surface, such as a fingerprint. The apparatus belongs to the category of livescan fingerprint scanners, as it directly acquires the image of a fingerprint in contact with a clear surface, bypassing the requirement for a staining fluid as found in conventional ink and roll procedures.

There is already a body of prior art concerning the inkless imaging of fingerprints. Most such systems utilize the critical angle phenomenon and/or the dual phenomenon of total internal reflection. A generic device which demonstrates readily both concepts is a right angle glass prism. A finger is placed on the hypotenuse or posterior surface of the prism, and optical pickup occurs along an axis in front of and perpendicular to one of the other two prism surfaces, denoted here as the front surface. This axis, when extended to the back surface, forms an angle with its normal which is greater than the critical angle of light entering the glass from a medium with unity index of refraction, such as air. When a finger is placed in contact with the posterior prism surface, air is trapped between the papillary valleys and glass, and all light arising from the papillary valleys which penetrates the glass is refracted away from the aforementioned perpendicular axis. Light scattered from regions of the finger (papillary ridges) in direct contact with the glass does not undergo such a degree of refraction, due to the absence of the air-glass interface. Light scattered from the papillary ridges can therefore find a path to the photodetector device. If no light is reflected internally off regions of the posterior surface in contact with air, then the papillary ridges will appear illuminated relative to parts of the contact surface underlying the papillary valleys, and the dominant operating principle is the critical angle effect. If illumination is provided such that light is (totally) internally reflected off regions of the posterior surface in contact with air, then the parts of the contact surface directly underlying the papillary valleys will appear more illuminated with respect to the papillary ridges, which tend to frustrate the total internal reflection by absorbing some light and by scattering the remainder omnidirectionally.

Devices have been proposed based upon this prism approach. A disadvantage of the flat posterior surface is that only a limited portion of the otherwise curved finger surface can make contact and hence be imaged. One method for circumventing this problem is to form a well, generally cylindrical, in the posterior surface of the prism. The well accommodates the curvature of the object to be imaged, yet has the drawback of providing poor visualization of those portions of the well whose normal vector forms a large angle with the normal vector of the front prism surface. In addition, distortion of the image occurs when the light rays emanating from the curved object surface are focused onto a flat detector surface.

Solutions to the problem of complete and distortion-free imaging of the cylindrical surface, while still using the critical angle effect or frustrated total internal reflection, have been proposed which depart from the use of a prism per se. At least one such method employs a cylindrical transparent platen into which is inserted the finger, and under and around which a light source and sensor device, together with a focusing mechanism, are revolved, resulting in the acquisition of modulated light corresponding to the pattern of papillary ridges and grooves. The light source is directed at such an angle to the cylindrical well that light from it is totally internally reflected toward the photodetector, excepting where the presence of a papillary ridge in contact with the well frustrates this effect.

A disadvantage of an assembly such as is mentioned in the foregoing paragraph is the necessity to revolve the light source and focusing lens in synchrony with the photodetector. The invention disclosed in this patent uses a stationary light source and focusing lens. Embodiments are discussed which allow the source to be positioned such as to yield an imaging system based on either the critical angle effect or on frustrated total internal reflection.

SUMMARY OF THE INVENTION

An object of this invention is to provide an effective and simple system for acquiring a high quality roll print from an individual finger. The process is to be achieved without the need for ink or other staining media. Potential applications include law enforcement and identity verification to enable access to privileged resources.

It is a further object of the invention to provide such a system wherein the image is front-projected along the central axis of the well, rather than recording light data beneath the well, the linear photodetector array being used to scan the image surface so as to trace a partial surface of revolution during the scanning process. The photodetector does not have to revolve directly about the well, thus allowing for reductions in size and complexity of the photodetector support structure.

A further advantage of this invention is the incorporation of a tapered well into which is inserted the object to be scanned. This feature serves two purposes, the first being that of improved optical performance regarding the front projection of rays emanating from the object. The second purpose of the tapered well is that the taper enables digits of varying sizes to be accommodated within it in such a way that proper contact is made between the surface of the well and the region of the digit that contains the surface structures to be imaged. This feature dispenses with the need to use wells of varying sizes to cover a wide range of finger sizes.

This invention also proposes to eliminate the need for special forms of illumination. The embodiments presented all utilize unfocused and uncollimated light sources.

The preferred embodiment of the invention utilizes a light source, a conical lens comprising a tapered well, a conical front surface, and an undersurface capable of passing illuminating light rays, a spherical focusing lens, and a linear photodetecting array capable of receiving focused light rays emerging from the interior surface of the tapered well. The axes of the tapered well, conical front surface, spherical focusing lens, and the axis of revolution of the photodetecting device are all coaxial along what shall be termed the central axis. A finger or thumb is placed in the conical well and moved forward until satisfactory contact is achieved between the surface of the digit and the surface of the well. The well lies on the upper side of the conical lens, and tapers in the forward direction (toward the photodetector). In one embodiment, a source of illumination is provided from underneath the conical lens, passing through the substrate of the lens and impinging upon the tapered well. The light source is positioned in such a relationship to the conical lens that no light reflecting off a point on the tapered well in contact with the air finds an optical path out the front conical surface and through the spherical focusing lens. However, when an object such as the ridge of a finger comes in direct contact with a point on the surface of the tapered well, some light scattering off that point passes through the conical lens substrate, and is projected forward toward the spherical focusing lens after it emerges from the conical front surface.

The light rays which reach the imaging lens from the surface of the tapered well, denoted as the object surface, are focused onto a second surface, denoted as the image surface. If the well surface is conical, apex toward the lens, then to within a first-order analysis (to be discussed in greater detail below) the image surface will also be a cone, whose axis is the central axis, the apex of the image cone also pointing in the forward direction. The image surface is scanned by a linear photodetector device, which traces out a partial revolution about the central axis so as to be able to image the entire angular extent of the well, typically 180° or more. At each angle in its rotary trajectory, the photodetector acquires an image of points on the tapered well surface lying along a line which intersects with the central axis. The angular increments must be small enough so as to insure adequate sampling (without aliasing) of all papillary features to be imaged. A mechanism useful for achieving this aim is a stepper motor. The functions of stepper motor and photodetector array can be synchronized under the control of a central processor.

BRIEF DESCRIPTION OF THE DRAWINGS

FIG. 6 depicts a lighting arrangement suitable for exploiting the critical angle effect.

FIG. 7 depicts an alternate lighting arrangement used to exploit total internal reflection.

DESCRIPTION OF THE PREFERRED EMBODIMENTS

Figure 1:
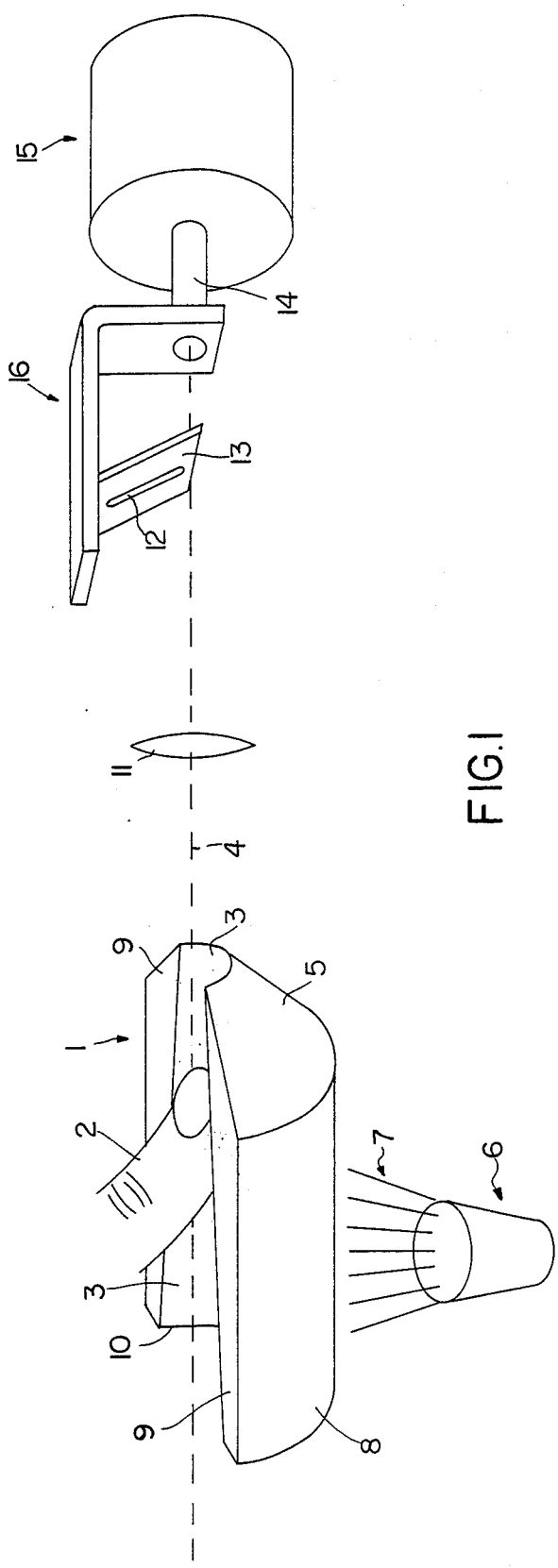
FIG. 1 is a perspective view of the invention components and their general physical relationships.
Figure 2:
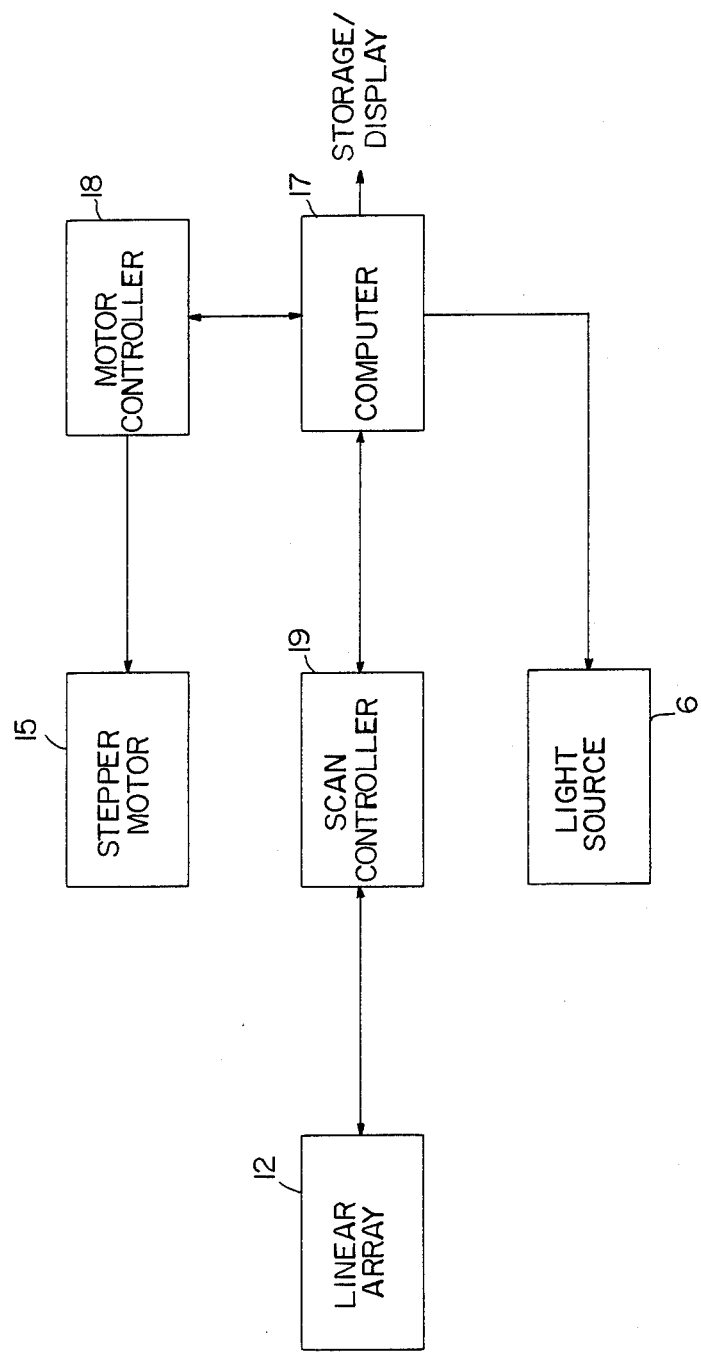
FIG. 2 is a system block diagram showing the logical relationships between the invention components so as to allow for the acquisition of data conveying detailed and accurate information about a single fingerprint pattern.
Figure 3:
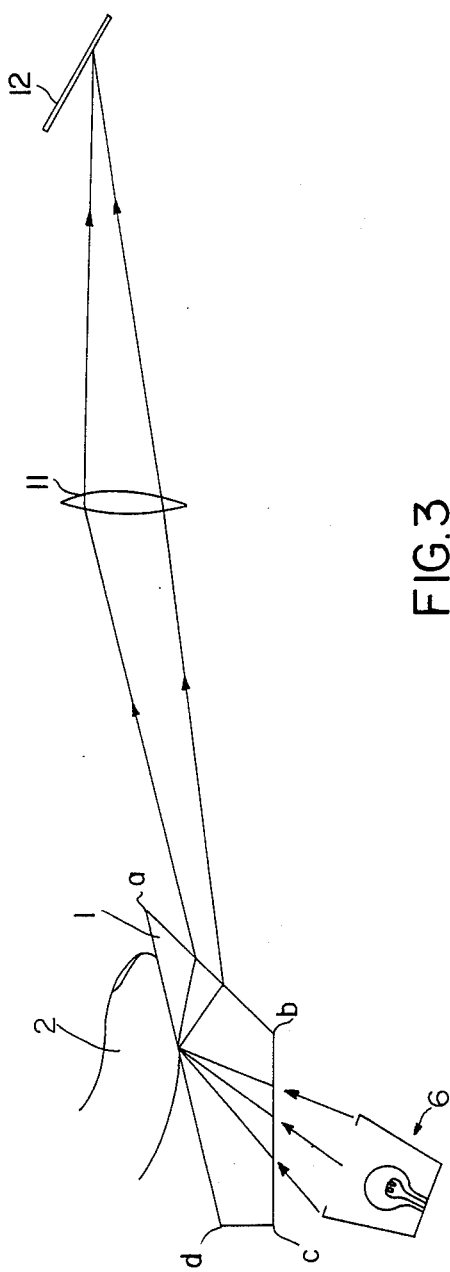
FIG. 3 shows a cutaway view of the invention to trace the paths of light rays that are scattered by a single target point and travel through the optics to the linear photodetector array.

The embodiments whose descriptions follow concern the following areas: general system design, conical lens design, and methods of illumination. Some consideration is given to the reduction or elimination of distortions arising from the fact that the lens law does not predict that a conical object projects perfectly into a conical image surface.

A conical lens 1, light source 6, spherical imaging lens 11 and linear photodetector array 12 set in motion along an arc by a stepper motor 15 comprise the major components of the apparatus. The photodiode array, stepper motor and light source are controlled by a computer 17. The light source, positioned beneath the side surface 8 of the conical lens 1, provides a source of illumination for the surface 3 of the well. In the FIG. 4 embodiment the tapered well is assumed to be conical, although, as shall be discussed later, other shapes may provide advantages. In one embodiment (FIG. 5) the light source is positioned in such a way that some light rays passing off the fingerprint ridges in contact with the surface of the well exit the front surface 5 of the conical lens and are focused by the imaging lens 11 onto the image surface, on which revolves the photodetector array 12. Light rays which are reflected off papillary valleys which have trapped air or a liquid of very low refractive index cannot find a path to the photodetector array 12.

The focusing lens 11 and stepper motor shaft 14 are centered on the central axis 4. Mounting bracket 16 and photodetector mount 3 are constructed so that as the motor shaft 14 rotates, the photodetector array 12 sweeps out a surface 4 corresponding to the image surface of the conical object surface. The linear photodetector array 12 is aligned in such a way that a line through its length intersects the central axis. The position of the stepper motor 15 is controlled by the motor controller 18, which in turn exchanges signals with the computer 17. The maximum allowable stepper angle $\theta$, maximum distance between pixels q, and maximum radius of the tapered well 3, $R_{max}$, are related by the simple expression:

$$\theta_{deg} = \frac{180}{\pi} \cdot \frac{q}{R_{max}}$$

For example, if one desires 300 pixels per inch resolution (0.0033 inch pixel spacing), for a conical well whose maximum radius is 0.50 inches, then the angular resolution of the stepper motor 15 must be no less than 0.38 degrees. One line of data corresponding to a line of pixels on the object surface which form a plane with the central axis is acquired for each angular position of the stepper motor 15. After the computer 17 receives data from the scan controller, the photodetector array 12 is revolved through another angular increment, and a new line of data is acquired. In this manner an entire image worth of data is made available for processing by the computer 17. The pixel data acquired from the completion of this scanning process are aligned along a polar coordinate grid. One task of the computer 17 is to reformat this data along the standard cartesian coordinate grid.

Figure 4:
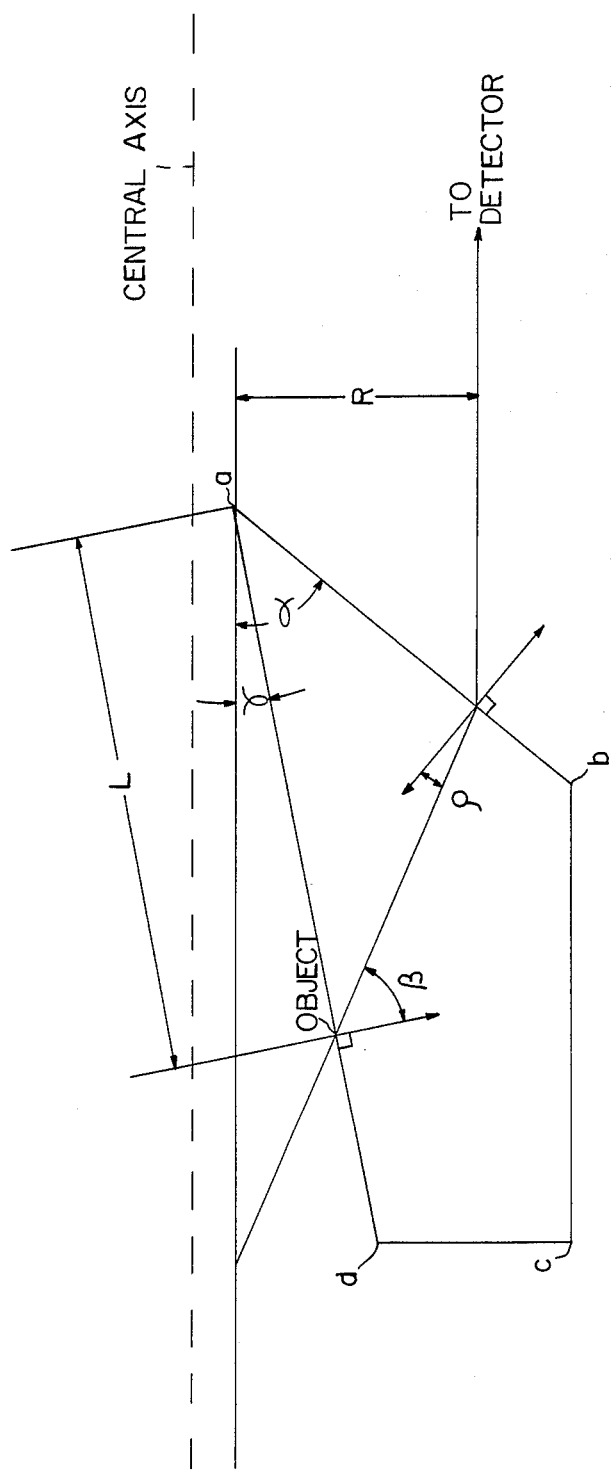
FIG. 4 defines the geometric quantities relevant to the application of simple ray theory to the design of the conical lens.

FIG. 4 illustrates the principles of design of a conical lens 1 containing a conical well. The conical lens can be regarded as the volume of revolution of surface abcd about the central axis. The angle of revolution may be 360°, but in preferred embodiments is less, being close to or at 180°. The following are the correspondences between line segments and surfaces of revolution: line ab and the front surface 5; line bc and the side surface 8; line cd and the rear surface 10; and line da and the well surface 3.

Surface 8 is not necessarily be a surface of revolution, but may instead be a single nonaxially symmetrical surface, or a combination of separate surfaces. Assuming that FIG. 4 is aligned such that the central axis is horizontal, then $\gamma$ is the angle between line ad and the horizontal, $\alpha$ is the angle between line ab and the horizontal, $\rho$ is the angle of refraction of a light ray horizontally entering the front surface, and $\beta$ is the angle which this refracted ray makes with the normal of line da.

The reverse of this path represents a light beam which is scattered from an object point on the surface of the well, and is depicted in FIG. 4. Denoting the index of refraction of the conical lens substrate by n, we have from Snell's law and the geometry:

$$\rho = \sin^{-1} \frac{\cos(\alpha)}{n}$$

and $\beta = \alpha + \rho - \gamma$. The quantities R, which is the distance of the horizontal ray from point a, and L, the distance from the object point to point a, are linearly related, their ratio being:

$$\frac{R}{L} = \frac{\sin(\gamma) \times (\cot(\gamma) + \tan(\alpha + \rho))}{\cos(\alpha) + \tan(\alpha + \rho)}$$

This ratio is important, as it measures the degree to which the line ad is compressed when projected forward by the front surface of the lens. The greater this ratio, the smaller one can make the imaging lens 11 before diffraction effects limit resolution.

Fixing $\alpha$ and $\gamma$ uniquely determines the other two angles and the ratio R/L. A further restraint is that $\beta$ be greater than the critical angle $\sin^{-1}(1/n)$. One design strategy is to fix Y to some desirable quantity, and to seek the $\alpha$ which maximizes R/L, while still yielding a permissible value of $\beta$. For example, if $n = 1.49$, $\gamma = 10°$, then $\alpha = 40°$ yields a maximum R/L of 0.364, in which case $\beta = 60.9°$, which is larger than the critical angle of 42.15°. Note that R/L increases with increasing $\gamma$. While a forward taper in the well 3 yields a positive $\gamma$, it is entirely possible to have no taper or a backward taper to the well 3.

Figure 5:
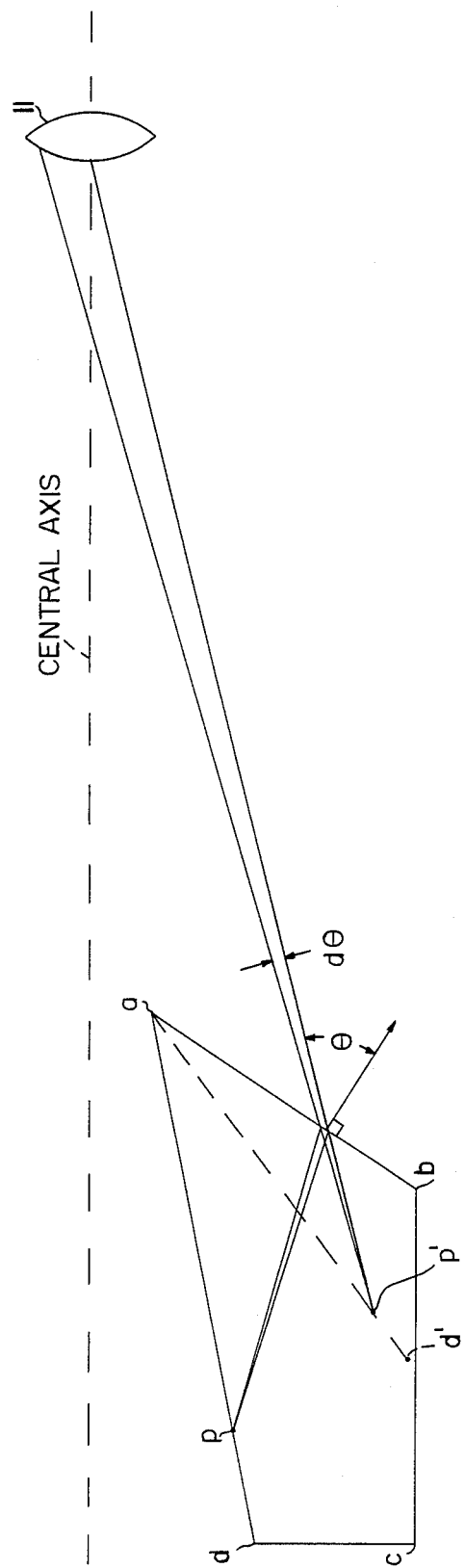
FIG. 5 illustrates the formation of a set of virtual object points from a set of object points.

FIG. 5 illustrates an important concept in the design of the system, namely, the creation of a set of virtual object points in correspondence with each actual object point. A virtual object point I corresponding to point P is formed by the intersection of almost parallel rays which originate from the imaging lens 11 and are refracted by front surface 5 toward point P. Such rays might be constructed from a single ray at angle of incidence onto surface 5 of $\theta$, and a second ray whose angle of incidence is $\theta + \delta\theta$, which $\delta\theta$ is an infinitesimal. Due to the finite expanse of the aperture of the imaging lens 11, $\theta$ varies, and hence there is a set of virtual object points corresponding to the single point p. The system must be constructed so that the images of the sets of virtual object points corresponding to the two resolvable object points must not overlap. One way to achieve this objective is to minimize the angular extent of the imaging lens 11 as seen from the conical lens 1, that is, by reducing the diameter of imaging lens 11 and/or increasing the distance between the conical lens 1 and imaging lens 11. An alternative is to introduce curvature into ab to provide better (virtual) convergence of rays exiting surface 5 which arise from a single object point.

Another factor to be considered is that curve va, which is the set of virtual object points as seen from the center of the imaging lens 11 of segment da, is only approximately linear. This, along with the simple fact that an imaging lens such as 11 only approximately maps a line segment such as that which passes through point a and I into a line, creates a need for a minimum amount of depth of focus. Depth of focus can always be improved by decreasing the diameter of the imaging lens 11 down to where the effects of diffraction begin to degrade system performance, and by increasing the distance between the imaging lens 11 and the conical lens 1. In addition, curvature into segment da in FIG. 4 can be introduced so that it yields a virtual object curve va whose image is linear. Lastly, the introduction of curvature into the photodetector array 12 can allow its surface of revolution to more closely match the image surface of the tapered well 3.

By suitable placement of the light source 6, the system can exploit either the critical angle effect or frustrated total internal reflection. In the FIG. 6 arrangement, light rays impinge upon the well surface 3 at an angle from the normal which is less than the critical angle. This yields an image of papillary ridges in contact with the surface of the well 3 based upon the critical angle effect previously described. FIG. 7 illustrates a variation of the conical lens 1 in which surface 8 tapers toward the back, allowing for light from source 6 to strike the well 3 at an angle beyond the critical angle. Light reaching a solid-air interface is totally internally reflected toward surface 5, whereas light reaching papillary ridges is scattered omnidirectionally, or absorbed.

Because a considerable amount of refraction is occurring in the optical system, especially regarding the bending of light rays as they emerge from surface 5, there exists a potential for problems involving chromatic aberration. This can be eliminated by the incorporation of a monochromatic light source 6. In addition, resolution will be improved by using the shortest practical wavelength. This, in conjunction with a narrow-band light filter placed along the optical path between the conical lens 1 and the photodetector array 12 and which passes light originating from the monochromatic source 6, will serve to eliminate the spurious effects of ambient light. Much of the ambient light can be prevented from entering the system by blackening surfaces 9 and 10, and by enclosing the system, excluding the well 3, in a light-proof fixture.

I claim:

1. Apparatus for acquiring the image of a fingerprint comprising:

a stationary conical lens formed of a solid transparent substrate and having a front surface in the shape of a partial cone tapering in a forward direction for allowing light rays interior to the conical lens to be refracted in said forward direction, and into which lens is formed a well, coaxial with said front surface along a central axis, into which well a finger to be imaged is placed, and which lens additionally possesses a side surface through which interrogating light rays may pass, the front surface and well together possessing the property that only light rays which arise off the surface of the well at an angle to its normal which is greater than the critical angle of light refracted through the air-substrate interface, emerge from said front surface and are refracted in said forward direction substantially, parallel to said central axis;

a stationary polychromatic light source for interrogating the object to be scanned such that light rays are directed through the substrate of the conical lens onto the internal surface of the well;

an imaging lens positioned such that it is coaxial with a central axis of the front conical surface and such that it creates a focused image surface of the well surface of the conical lens;

a photodetector array for converting light signals focused by the imaging lens into electrical signals corresponding to the image of papillary ridges and valleys of a finqer positioned in the well of the conical lens;

a means for positioning the photodetector array such that it is tangential to the image surface of the well and such that a line through the endpoints of the array intersects the central axis;

a means for rotating the photodetector array such that the aforementioned relationship to the central axis is preserved, and such that it sweeps out in steps a surface of revolution corresponding to the image surface of the well in the conical lens;

a means for acquiring the electrical data generated by the photodetector array and processing the data in such a way as to create a complete fingerprint image for subsequent display and storage.

2. The apparatus of claim 1, wherein said well is tapered in said forward direction.

3. The apparatus of claim 2, wherein said well is tapered in a conical shape.

4. The apparatus of claim 2, wherein said well is tapered in such a fashion as to yield an image which is substantially conical.

5. The apparatus of claim 1, wherein said front surface is curved for improvement in the imaging system point spread function.

6. The apparatus of claim 1, wherein the photodetector array is curved to match the image surface of the well.

7. The apparatus of claim 1, wherein the light source is positioned such that illuminating rays pass through the substrate of the conical lens and impinge upon the well surface at an angle to its normal which is less than the critical angle of light refracted through an air-substrate interface, for causing light from papillary ridges, to be scattered omnidirectionally and to traverse a path out the front surface of the conical lens to be focused on the photodetector array, and for causing light from papillary valleys to be refracted at the air-substrate interface in such a manner that no such light traverses a path to the photodetector array.

8. The apparatus of claim 1, wherein the light source is positioned such that illuminating rays pass through the substrate of the conical lens and impinge upon the well surface at an angle to its normal which is greater than said critical angle for causing light emitted from the source to be totally internally reflected off points on the well in contact with air and to travel out the front surface of the conical lens and to be focused onto the photodetector array, and for causing illuminating light which impinges upon a point on the well in contact with a papillary ridge to be scattered omnidirectionally, such that only a small fraction of said scattered illuminating light exits the front surface of the conical lens to be focused onto the photodetector.

9. The apparatus of claim 1, 7 or 8, wherein the source of illuminating rays is monochromatic.

10. The apparatus of claim 1, 7 or 8, including a narrowband light filter is positioned along the optical path between the conical lens and photodetector, said filter for admitting light rays in the frequency range of the monochromatic light source and for rejecting light of other frequencies.

11. The apparatus of claim 9, including a narrowband light filter positioned along the optical path between the conical lens and photodetector, said filter for admitting light rays in the frequency range of the monochromatic light source and for rejecting light of other frequencies.

* * * * *